US012613124B2

(12) United States Patent
Kobayashi

(10) Patent No.: US 12,613,124 B2
(45) Date of Patent: Apr. 28, 2026

(54) LARGE WEIGHT SCALE FOR DETECTING POSSIBILITY OF BEDSORE, AND BEDSORE DETECTING METHOD

(71) Applicant: A&D COMPANY, LIMITED, Tokyo (JP)

(72) Inventor: Hayato Kobayashi, Saitama (JP)

(73) Assignee: A&D COMPANY, LIMITED, Tokyo (JP)

( * ) Notice: Subject to any disclaimer, the term of this patent is extended or adjusted under 35 U.S.C. 154(b) by 356 days.

(21) Appl. No.: 18/225,515

(22) Filed: Jul. 24, 2023

(65) Prior Publication Data

US 2024/0035877 A1 Feb. 1, 2024

(30) Foreign Application Priority Data

Jul. 28, 2022 (JP) ................................. 2022-120737

(51) Int. Cl.
| | |
|---|---|
| *G01G 19/44* | (2006.01) |
| *A61B 5/00* | (2006.01) |
| *G01G 19/52* | (2006.01) |

(52) U.S. Cl.
CPC ............. *G01G 19/44* (2013.01); *A61B 5/447* (2013.01); *A61B 5/746* (2013.01); *G01G 19/52* (2013.01)

(58) Field of Classification Search
CPC ........ G01G 19/44; G01G 19/52; A61B 5/447; A61B 5/746; A61B 5/445
USPC .......................................................... 177/1
See application file for complete search history.

(56) References Cited

U.S. PATENT DOCUMENTS

| | | | | |
|---|---|---|---|---|
| 6,875,932 | B2 * | 4/2005 | Tuft ....................... | G01G 19/44 |
| | | | | 177/144 |
| 7,030,764 | B2 * | 4/2006 | Smith .................... | A61B 5/1115 |
| | | | | 340/666 |
| 9,814,637 | B2 * | 11/2017 | Sazonov .............. | A61G 5/1043 |
| 11,076,777 | B2 * | 8/2021 | Lee ....................... | A61B 5/0024 |
| 2017/0150905 | A1 * | 6/2017 | Shen .................. | G08B 21/0453 |
| 2019/0374133 | A1 * | 12/2019 | Shen .................. | G08B 21/0446 |

FOREIGN PATENT DOCUMENTS

| | | | | |
|---|---|---|---|---|
| JP | 2018004377 A | 1/2018 | | |
| JP | 7154730 B | 10/2022 | | |
| WO | WO 2019073735 A1 * | 4/2019 | ........... | H04M 11/00 |
| WO | WO-2020103535 A1 * | 5/2020 | ........... | G01G 19/44 |
| WO | 2022158438 A1 | 7/2022 | | |

* cited by examiner

*Primary Examiner* — Jacques M Saint Surin
(74) *Attorney, Agent, or Firm* — Studebaker Brackett PLLC

(57) ABSTRACT

Provided is a large weight scale capable of weighing a to-be-weighed subject sitting in a wheelchair, including a rectangular weighing base on which the to-be-weighed subject gets on, weighing sensors disposed at four corners of the weighing base, and a control unit configured to perform arithmetic operations based on output values of the weighing sensors, wherein the large weight scale includes a bedsore detecting unit configured to detect and make a notification of the possibility of the to-be-weighed subject in a wheelchair developing a bedsore based on a first sum value of output values of a pair of the weighing sensors disposed on a left side of the weighing base, a second sum value of output values of a pair of the weighing sensors disposed on a right side of the weighing base, and a third sum value of output values of all of the weighing sensors.

5 Claims, 8 Drawing Sheets

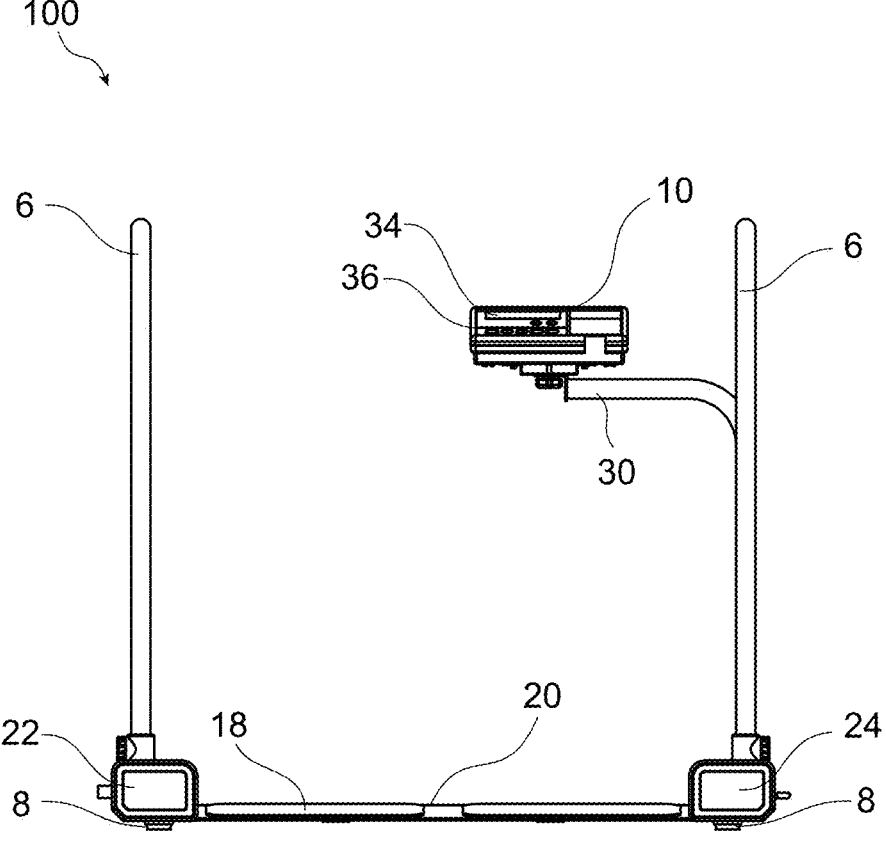
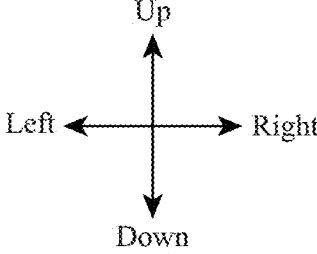
FIG. 2

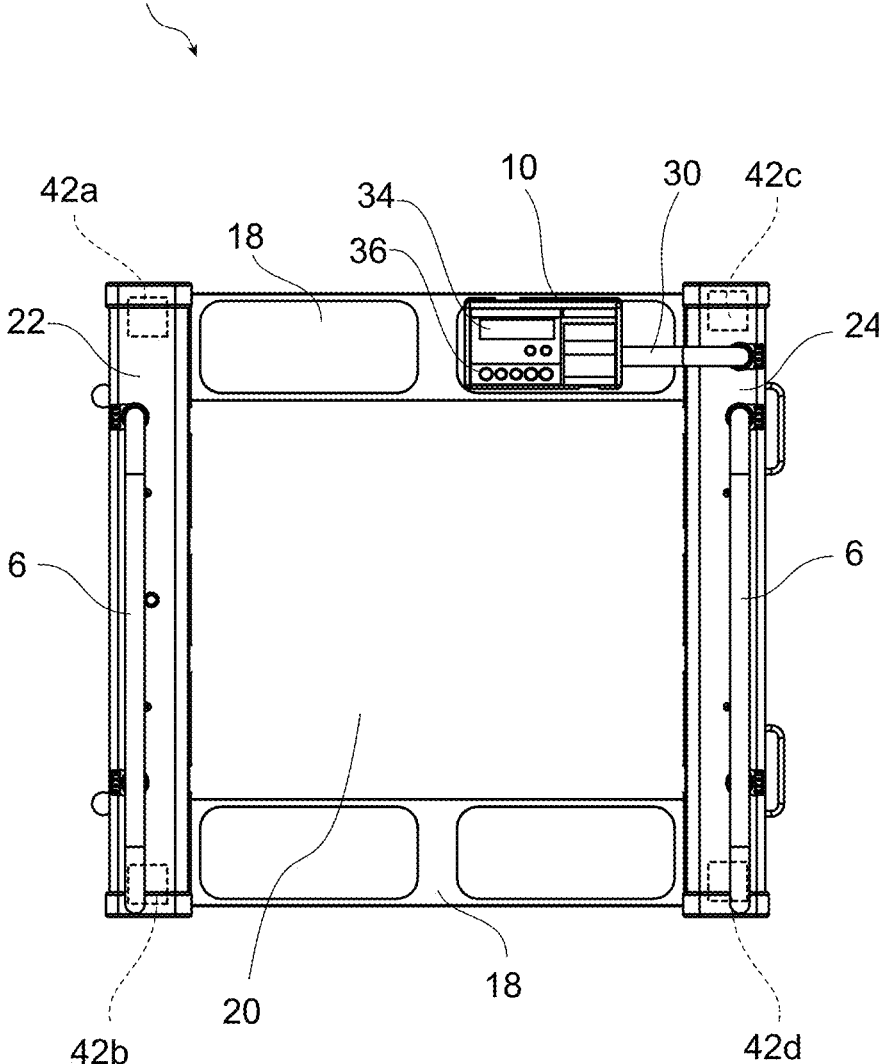
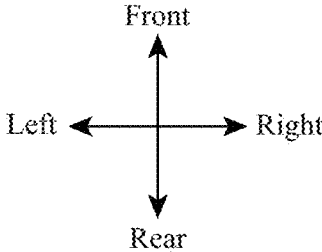
FIG. 3

100

FIG. 6A  Not biased
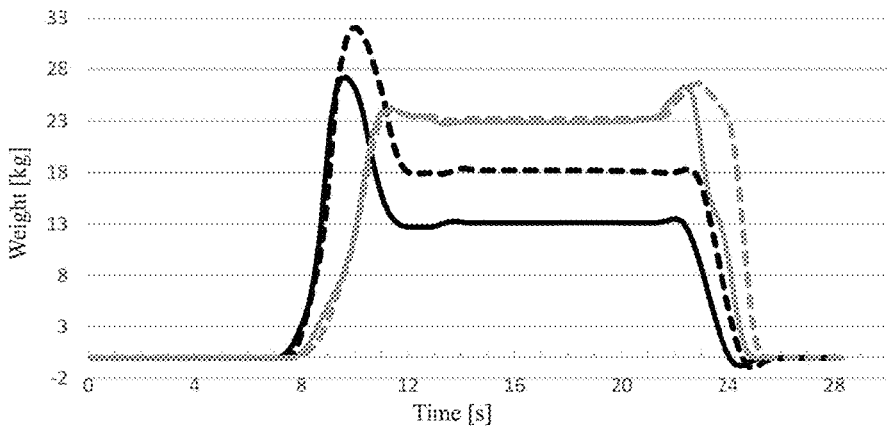
FIG. 6B  Biased to right
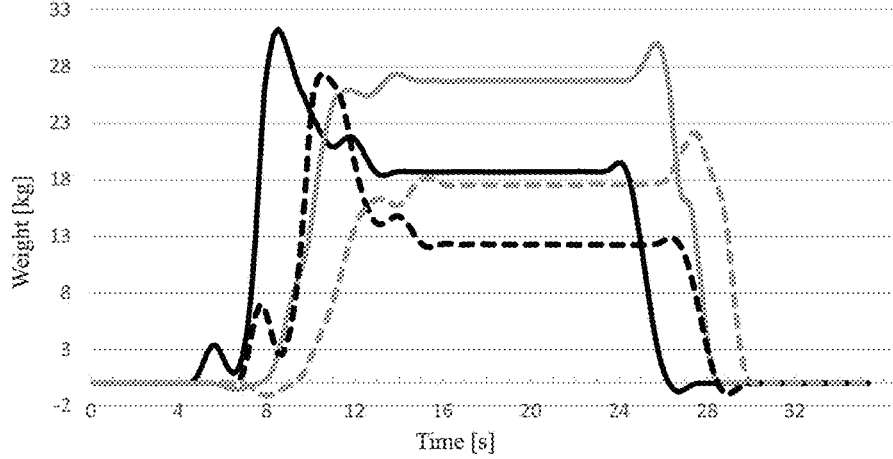
FIG. 6C  Biased to left
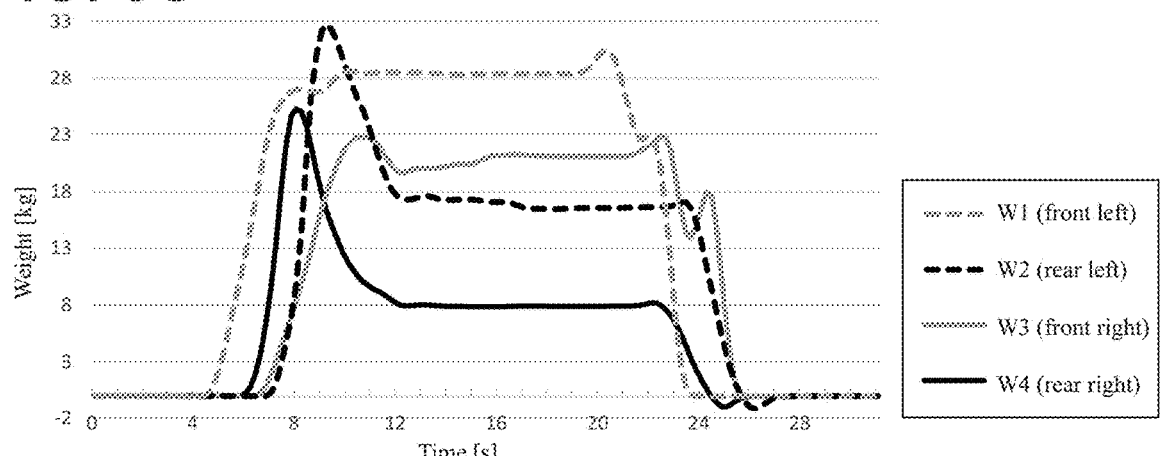

FIG. 7A   Not biased
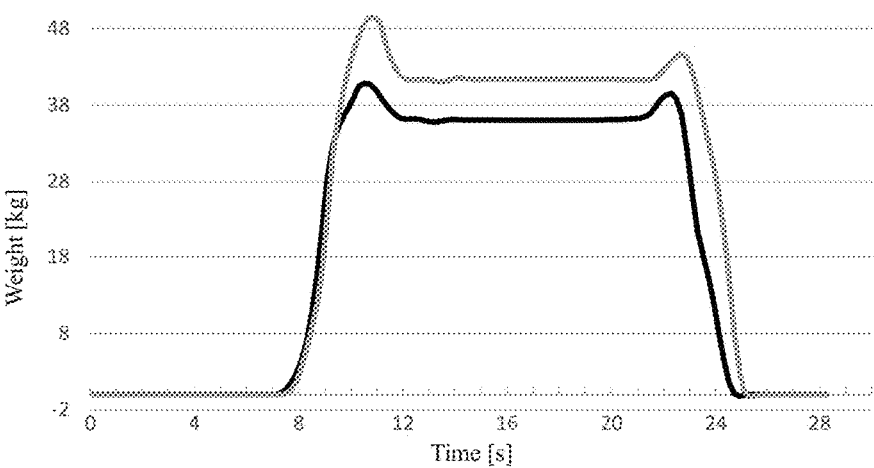
FIG. 7B   Biased to right
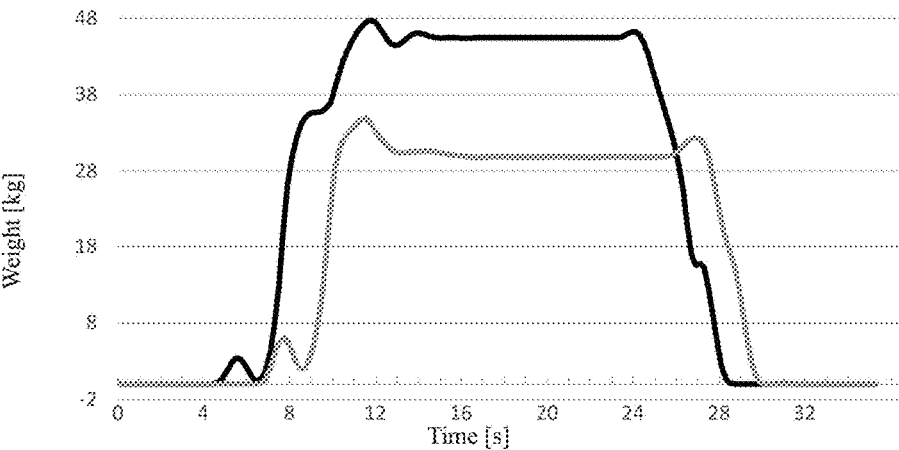
FIG. 7C   Biased to left
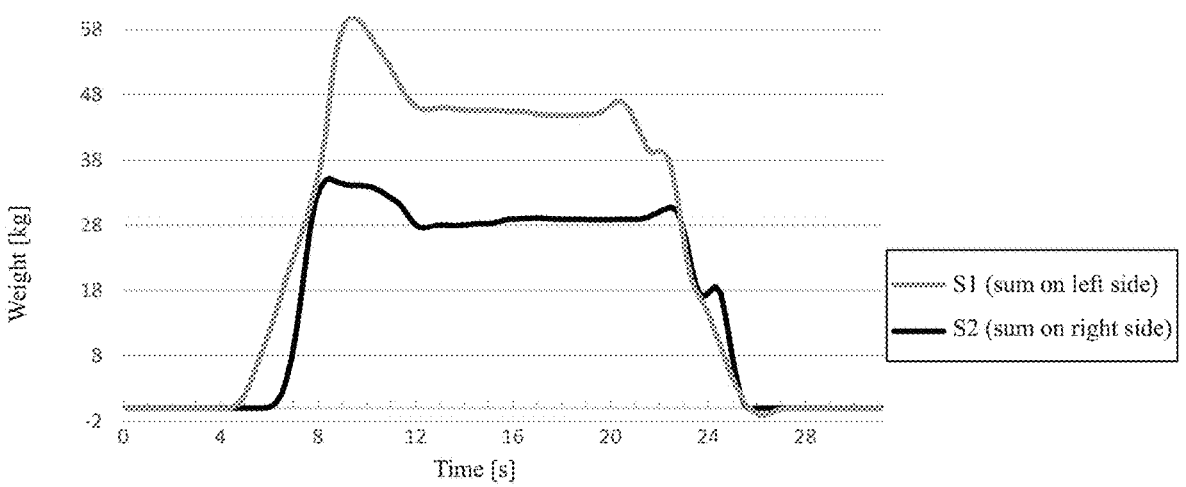

LARGE WEIGHT SCALE FOR DETECTING POSSIBILITY OF BEDSORE, AND BEDSORE DETECTING METHOD

TECHNICAL FIELD

The present invention relates to a large weight scale capable of weighing a to-be-weighed subject sitting in a wheelchair, and particularly to a large weight scale that detects the possibility of a to-be-weighed subject in a wheelchair developing a bedsore, and a bedsore detecting method.

BACKGROUND ART

A bedridden person is often forced to stay in the same body position, and a load is therefore likely to concentrate on a specific portion, so that the person sometimes develops a pressure ulcer, a so-called bedsore. There are also cases where such a person cannot recognize pain from placing pressure on their body as a result of his/her own body weight and/or cannot move by himself/herself, and the person needs to be cared for by another person so as to change their posture, however, it is difficult for the other person to grasp where the pressure is being placed. Therefore, a bed that detects an on-bed state of a person lying in bed has been disclosed (for example, Patent Literature 1).

In Patent Literature 1, a plurality of load sensors are provided on a bed main body, and by detecting changes in a load applied to the bed, a state of a user on a bed surface of the bed main body is detected.

CITATION LIST

Patent Literature

Patent Literature 1: Japanese Published Unexamined Patent Application No. 2018-4377

SUMMARY OF INVENTION

Technical Problem

Such a bedsore problem is particularly notable with a person who lies on a bed over a long period of time, but likewise occurs also with a person who uses a wheelchair. The risk of developing a bedsore increases if a person does not sit in a correct posture in a wheelchair for a long period of time. However, the bed disclosed in Patent Literature 1 is not used for wheelchair users. Moreover, specialized equipment such as the bed disclosed in Patent Literature 1 is much more expensive than conventional beds. Rather than using such expensive specialized equipment, it has been desired to easily know when a person is out of the correct posture while a to-be-weighed subject is sitting in a conventional wheelchair.

Here, in the case of a large weight scale to be used in medical facilities, a to-be-weighed subject can get on the weighing base together with a wheelchair, and a weight of the to-be-weighed subject sitting in the wheelchair can be weighed. When weighing of the weight made with the weight scale while the subject is in a wheelchair can detect whether the subject is in a correct posture, the subject can be notified of sitting out of the correct posture in the wheelchair, and can be urged to sit with a correct posture in the wheelchair. In addition, when it is possible for a caregiver to know that the to-be-weighed subject is out of the correct posture where a bedsore is likely to develop, the caregiver can give care to ease to-be-weighed subject into a comfortable posture.

The present invention was made in view of these circumstances, and provides a large weight scale for detecting that a person sitting in a wheelchair is out of the correct posture, that is, detecting whether a person in a wheelchair is likely to develop a pressure ulcer.

Solution to Problem

In order to solve the problem described above, an aspect of the present disclosure provides a large weight scale capable of weighing a to-be-weighed subject sitting in a wheelchair, including a rectangular weighing base on which the to-be-weighed subject gets on, weighing sensors disposed at four corners of the weighing base, and a control unit configured to perform arithmetic operations based on output values of the weighing sensors, wherein the large weight scale includes a bedsore detecting unit configured to detect and make a notification of the possibility of the to-be-weighed subject in a wheelchair developing a bedsore based on a first sum value of output values of a pair of the weighing sensors disposed on a left side of the weighing base, a second sum value of output values of a pair of the weighing sensors disposed on a right side of the weighing base, and a third sum value of output values of all of the weighing sensors.

Further, in an aspect, the bedsore detecting unit is configured to determine and make a notification that there is the possibility of developing a bedsore when an absolute value of a ratio of a difference value between the first sum value and the second sum value to the third sum value exceeds a predetermined value.

Further, in an aspect, the bedsore detecting unit is configured to make a notification as to whether there is the possibility of developing a bedsore on the left side of the body or the right side of the body of the to-be-weighed subject.

Further, in an aspect, the bedsore detecting unit is configured to determine whether the to-be-weighed subject is in a wheelchair.

Further, a method of detecting the possibility of a to-be-weighed subject developing a bedsore according to an aspect of the present disclosure is a method of detecting the possibility of a to-be-weighed subject in a wheelchair developing a bedsore by using a large weight scale provided with weighing sensors disposed at four corners of a rectangular weighing base on which a to-be-weighed subject gets on, and capable of weighing the to-be-weighed subject sitting in a wheelchair, and is configured so that a first sum value of output values of a pair of the weighing sensors disposed on a left side of the weighing base, a second sum value of output values of a pair of the weighing sensors disposed on a right side of the weighing base, and a third sum value of output values of all of the weighing sensors are calculated, and when an absolute value of a ratio of a difference value between the first sum value and the second sum value to the third sum value exceeds a predetermined value, it is determined and notified that there is the possibility of the to-be-weighed subject developing a bedsore.

Advantageous Effects of Invention

As is clear from the description given above, a large weight scale that detects the possibility of a to-be-weighed subject in a wheelchair developing a bedsore can be provided.

BRIEF DESCRIPTION OF DRAWINGS

FIG. 2 is a back view of the same weight scale.

FIG. 3 is a plan view of the same weight scale.

FIGS. 6A, 6B, and 6C are graphs of test data, illustrating output values.

FIGS. 7A, 7B, and 7C are graphs of test data, illustrating first sum values and second sum values.

DESCRIPTION OF EMBODIMENTS

Hereinafter, specific embodiments of a configuration of the present disclosure will be described with reference to the drawings. The embodiments do not intend to limit the present invention but are by way of illustration, and all features described in the embodiments and combinations thereof are not always essential for the invention.

Embodiment

Figure 1:
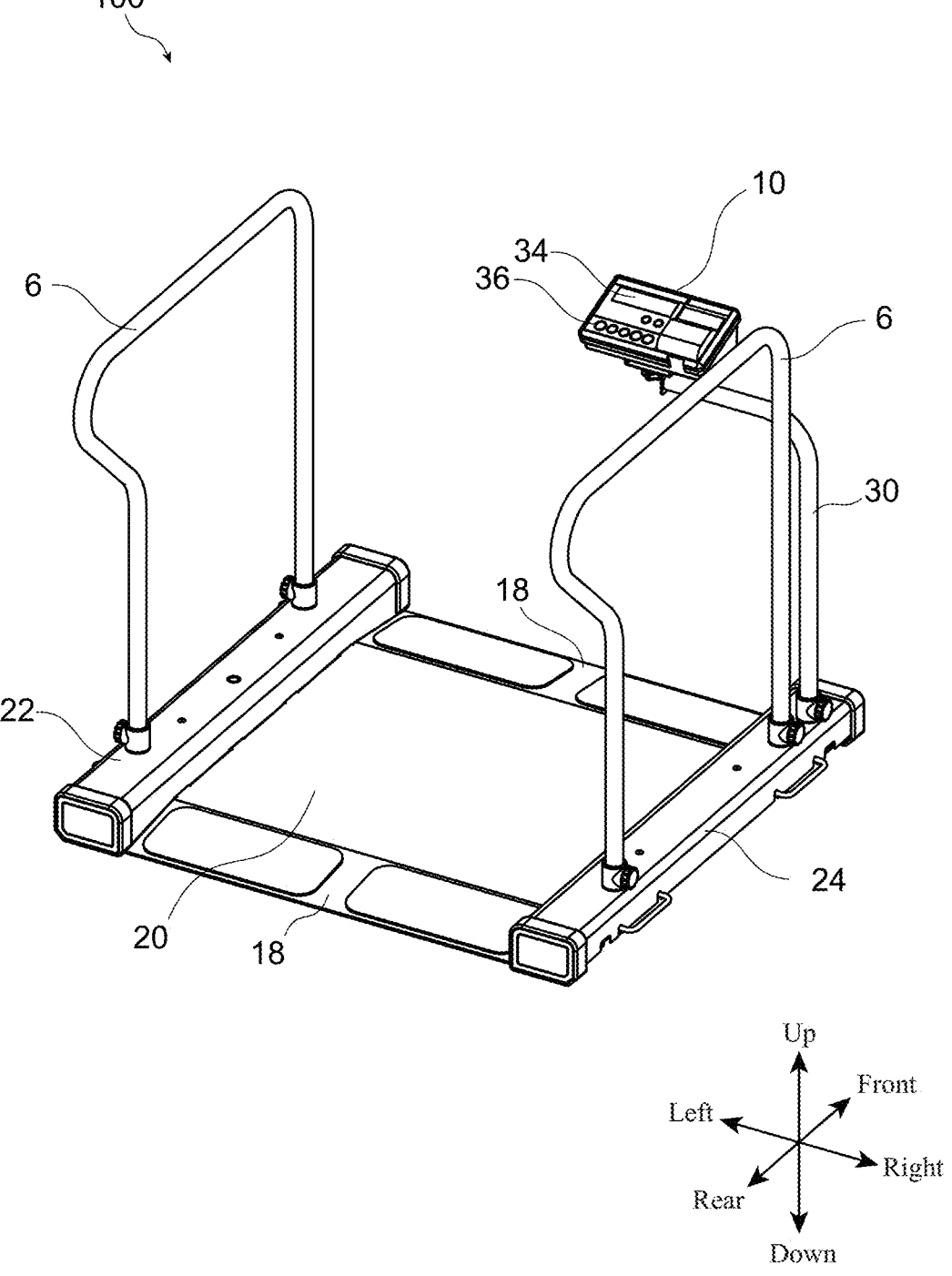
FIG. 1 is a perspective view of a weight scale according to a preferred embodiment of a configuration of the present disclosure.
Figure 4:
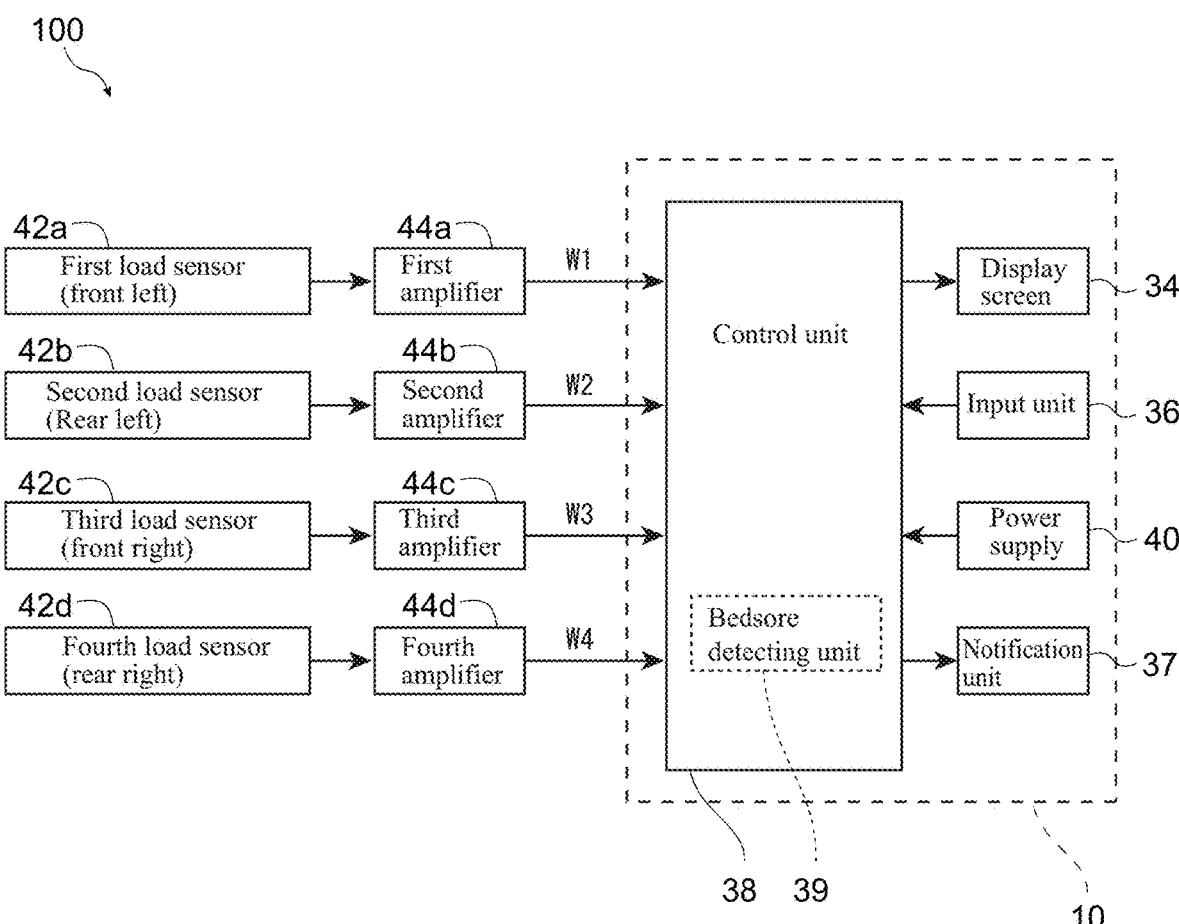
FIG. 4 is a control block diagram of the same weight scale.

A preferred embodiment according to a configuration of the present disclosure will be described with reference to the drawings. FIG. 1 is a perspective view of a weight scale 100 according to the embodiment. FIG. 2 is a front view of the weight scale 100. FIG. 3 is a plan view of the weight scale 100. FIG. 4 is a block diagram of a control system of the weight scale 100.

As illustrated in FIG. 1, the weight scale 100 is a large weight scale for medical use, and is configured so as to not only measure a weight of a to-be-weighed subject directly getting on the weight scale, but also to measure a weight of a to-be-weighed subject sitting in a wheelchair.

The weight scale 100 includes a weighing base 20 to which a to-be-weighed load is placed and applied, legs 8, handrails 6, and a display 10.

The weighing base 20 is formed into a large rectangular shape, and is configured so that, in order for a to-be-weighed subject to safely get on it, an upper surface serving as a step surface is wide, and the entirety is thin. The weighing base 20 is structured to have sufficient rigidity, and is configured by sandwiching, for example, a honeycomb-like reinforced plate (not illustrated) by an iron-made frame body and iron plates.

In order to allow a to-be-weighed subject in a wheelchair to get on the weighing base 20 while sitting in the wheelchair, at both front and rear end portions of the weighing base 20, gentle slopes 18 and 18 continued to the floor surface are provided. Moreover, each slope 18 is provided with a slip resistance so as to prevent a to-be-weighed subject from slipping when getting on and off the scale.

To both left and right ends of the weighing base 20, a left side bar 22 and a right side bar 24 are joined. Each side bar 22, 24 is formed into a hollow columnar shape, and wirings and an electronic substrate are housed inside. On upper surfaces of the side bars 22 and 24, the handrails 6 are attached so that a to-be-weighed subject who has trouble or difficulty walking can hold onto the handrails 6 to stand up.

Further, on an upper surface of one side bar (the right side bar 24 in the present embodiment) of the side bars 22 and 24, a pole 30 is detachably and turnably attached beside the handrail 6. The pole 30 is erected vertically and then bent to be horizontal, and to its tip end, the display 10 is attached.

On the display 10, a display screen 34 and an input unit 36 are provided. The display screen 34 is, for example, a liquid crystal display. The display screen 34 displays, for example, setting conditions, weighing results, data on the possibility of a to-be-weighed subject developing a bedsore to be described later, etc., and other displays necessary for settings.

The input unit 36 is, for example, key switches. With the key switches, a weighing operator can make various settings and commands of, for example, "tare subtraction," "weighing value outputting," and "zero point resetting." The display screen 34 and the input unit 36 may be integrally configured and provided as a touch panel type input unit 36.

Inside the display 10, a control unit 38 for performing various arithmetic processings and a power supply (battery, etc.) 40 are also provided. As illustrated in FIG. 4, the display 10 may further include a notification unit 37 as an information notification means such as an LED indicating a state by a light emitting pattern, a buzzer, or a speaker for outputting sound or voice. A form may be employed in which the display screen 34 doubles as the notification unit 37 by making the display screen 34 display notification information.

The legs 8 are provided on a lower surface of each side bar 22, 24. The legs 8 are disposed at both ends of each side bar 22, 24, that is, at the respective corners of the weighing base 20. Between the respective legs 8 and the side bars 22 and 24, weighing sensors 42a to 42d are provided, and the weighing base 20 is supported through these weighing sensors 42a to 42d.

Here, the far side of the weight scale 100 is defined as the front side, and the near side is defined as the rear side, and a first weighing sensor 42a provided at the front side of the left side bar 22 (front left side of the weighing base 20), a second weighing sensor 42b provided at the rear side of the left side bar 22 (rear left side of the weighing base 20), a third weighing sensor 42c provided at the front side of the right side bar 24 (front right side of the weighing base 20), and a fourth weighing sensor 42d provided at the rear side of the right side bar 24 (rear right side of the weighing base 20), are collectively referred to as weighing sensors 42 unless specified otherwise.

The weighing sensors 42 are sensors to measure a load applied to the weighing base 20, and for example, a load cell is used. The weighing sensors 42a to 42d are configured to make outputs individually, and the outputs can be amplified by amplifiers 44a to 44d and transmitted to the control unit 38 inside the display 10. The configuration of the weighing sensors 42 is not particularly limited, and for example, a load cell is used. Although not illustrated, a specific configuration of the weighing sensors 42 is such that four gauges are affixed to four thin-walled portions of a strain body of a Roberval load cell, and the four gauges are connected so as to configure a bridge circuit, and the respective output values (data not converted into a weighed value and not subjected to arithmetic processing) can be judged by the control unit 38. Not only the configuration of the weighing sensors 42 but the shape of the strain body is also not particularly limited, and a conventionally known configuration such as a column type, a Roberval type, or a ring type may be used.

The control unit 38 is a microcomputer configured by mounting at least a CPU and a memory on an integrated circuit, and performs arithmetic processing based on a program stored in the memory. Mainly, based on output values W1 to W4 from the weighing sensors 42a to 42d, the control unit 38 performs a control to calculate a weighed value of a to-be-weighed object on the weighing base 20 and display the weighed value on the display screen 34.

The weight scale 100 includes a bedsore detecting unit 39 that detects the possibility of a to-be-weighed subject in a wheelchair developing a bedsore. Specifically, a state where the to-be-weighed subject is in a posture that is out of a correct sitting posture without bias on a seating surface of the wheelchair, that is, an ideal posture in which a bedsore is unlikely to develop, and that the current posture, if kept by the to-be-weighed subject, makes the possibility of the to-be-weighed subject developing a bedsore higher than in a normal state, is detected as "there is the possibility of a bedsore."

The bedsore detecting unit 39 is stored as a program in the memory of the control unit 38, and is configured software-wise in the control unit 38. The output values of the weighing sensors 42 input to the control unit 38 and data in the memory, etc., are also provided to the bedsore detecting unit 39. The bedsore detecting unit 39 performs arithmetic processing based on output values W1 to W4 of the weighing sensors 42a to 42d, and when there is the possibility of a bedsore, this is displayed on the display screen 34, or a notification of the possibility of a bedsore is made by sound or light by controlling the notification unit 37.

(Detecting Method)

The bedsore detecting unit 39 detects the possibility of the to-be-weighed subject developing a bedsore based on a first sum value S1 that is a sum of the output values W1 and W2 of a pair of weighing sensors 42a and 42b disposed on the left side of the weighing base 20, a second sum value S2 that is a sum of the output values W3 and W4 of a pair of weighing sensors 42c and 42d disposed on the right side, and a third sum value S3 that is a sum of the output values of all weighing sensors 42a to 42d. Specifically, first, the bedsore detecting unit 39 operates the first sum value S1, the second sum value S2, and the third sum value S3, and calculates a left-right ratio R1 as a ratio of a difference value between the first sum value S1 and the second sum value S2 to the third sum value S3. When an absolute value of the left-right ratio R1 exceeds a predetermined value, it is judged that there is the possibility of a bedsore.

The bedsore detecting unit 39 displays the left-right ratio R1 on the display screen 34, and when the absolute value of the left-right ratio R1 exceeds a predetermined value, judges that there is the possibility of a bedsore, and controls the display 10 so as to display that there is the possibility of a bedsore on the display screen 34. The notifying method when the possibility of a bedsore is detected is not limited to displaying on the screen, and a notification of the possibility may be given to a weighing operator by outputting sound or voice or turning on or flashing light (LED) by the notification unit 37.

The predetermined value is preferably in a range of 0.1 to 0.2, and more preferably 0.13 to 0.15. In the tests to be described later, etc., as an example, the predetermined value is set to 0.15, and when the absolute value of the left-right ratio R1 is 0.15 or more, it is judged that there is the possibility of the to-be-weighed subject developing a bedsore. That is, when –0.15<left-right ratio R1<0.15, no bedsore is detected, and when left-right ratio R1≤–0.15 or left-right ratio R1≥0.15, it is judged that there is the possibility of the to-be-weighed subject developing a bedsore. The left-right ratio R1 is calculated by calculating a difference value by subtracting the sum (second sum value S2) of output values of the pair of weighing sensors 42c and 42d on the right side from the sum (first sum value S1) of output values of the pair of weighing sensors 42a and 42b on the left side, and dividing the difference value by the sum (third sum value S3) of all output values. Therefore, when the left-right ratio R1 is positive, it is judged that there is a possibility of developing a bedsore on the left side of the body of the to-be-weighed subject, such as on the left buttocks, left thigh, or the back of the left knee, and when the left-right ratio R1 is negative, it is judged that there is the possibility of developing a bedsore on the right side of the body of the to-be-weighed subject, such as on the right buttocks, right thigh, or the back of the right knee. The bedsore detecting unit 39 may also make a notification as to whether there is the possibility of developing a bedsore on the left side of the body or the right side of the body of the to-be-weighed subject. A configuration may be made so that the left-right ratio R1 is universally displayed on the display screen 34 regardless of whether there is the possibility of a bedsore.

(Control Flow)

Figure 5:
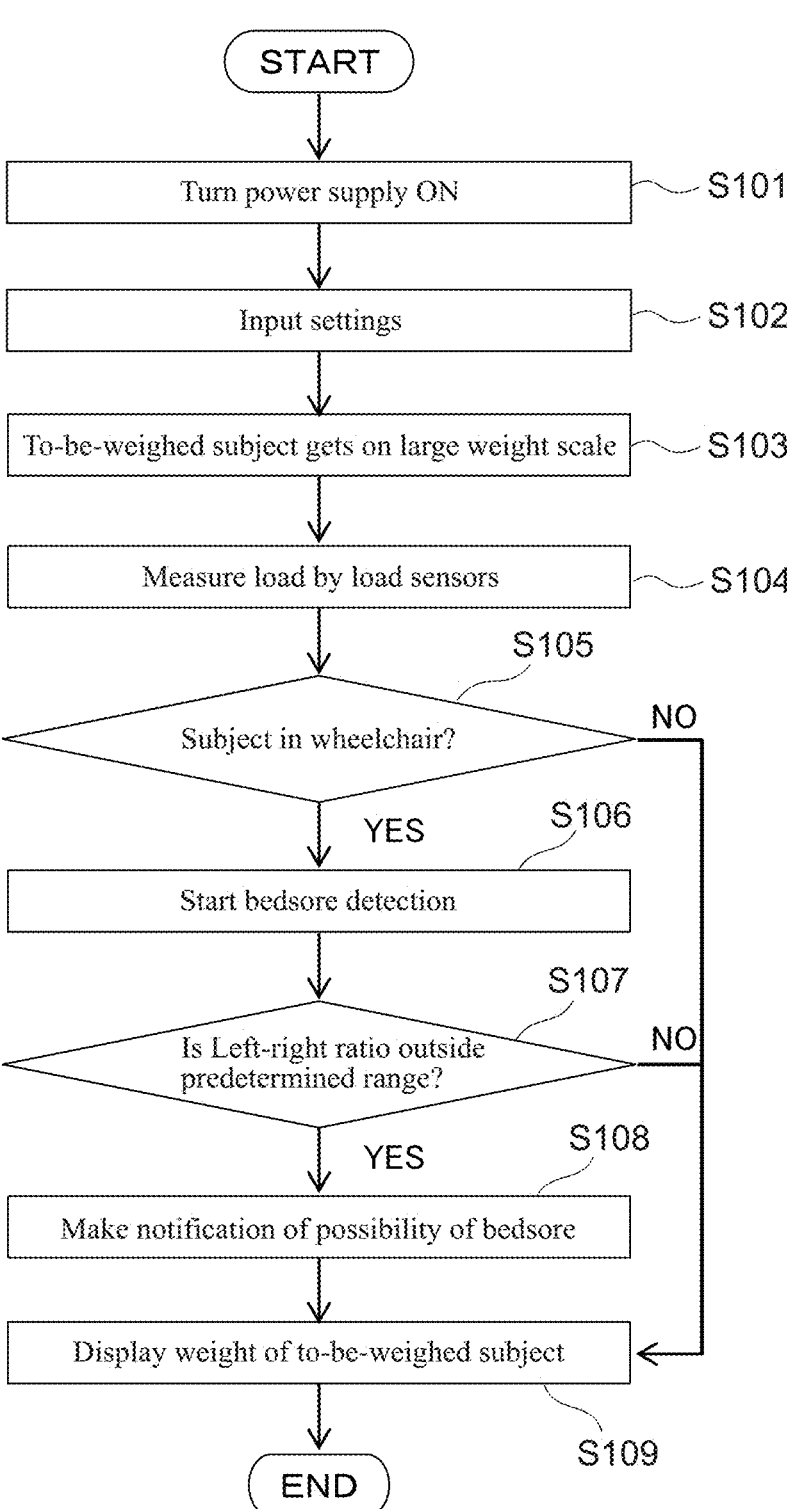
FIG. 5 illustrates a flow of bedsore detection.

FIG. 5 illustrates an example of a control flow of bedsore detection.

As illustrated in FIG. 5, first, in Step S101, the power supply of the weight scale 100 is turned on.

Next, the processing shifts to Step S102, and zero-point resetting and setting of tare subtraction, etc., are made. When tare subtraction is performed, a numeric value corresponding to the mass of clothing and the wheelchair, etc., to be subtracted is set.

Next, the processing shifts to Step S103, and the to-be-weighed subject gets on the weight scale 100. When the to-be-weighed subject is a wheelchair user, by using the slope 18, the to-be-weighed subject gets onto the weighing base 20 together with the wheelchair.

Next, the processing shifts to Step S104, and the weighing sensors 42a to 42d measure a load.

Next, the processing shifts to Step S105, and whether the to-be-weighed subject on the weighing base 20 is in a wheelchair is determined. Specifically, the bedsore detecting unit 39 determines that the to-be-weighed subject is in a wheelchair when the value of tare to be subtracted is a predetermined value or more (in the present embodiment, 13 kg or more). A configuration may be made in which whether to weigh the to-be-weighed subject while the subject stays sitting in a wheelchair is set by using the input unit 36 in Step S102. When the to-be-weighed subject is in a wheelchair, the processing shifts to Step S106. When the to-be-weighed subject is not in a wheelchair, the processing shifts to Step S109.

When the to-be-weighed subject is in a wheelchair, the processing shifts to Step S106, and a bedsore detection is started. The bedsore detecting unit 39 calculates a left-right ratio R1 based on output values W1 to W4 input from the weighing sensors 42a to 42d.

Next, the processing shifts to Step S107, and whether the value of the left-right ratio R1 is within a predetermined range is judged. When the left-right ratio R1 is outside the predetermined range, it is judged that there is the possibility of a bedsore, and the processing shifts to Step S108. As an example, when a judgment value of the left-right ratio is set to 0.15, being outside the predetermined range means that an absolute value of the left-right ratio R1 is 0.15 or more. When the value of the left-right ratio R1 is within the predetermined range, the processing shifts to Step S109.

When the absolute value of the left-right ratio R1 is equal to or more than the predetermined value, the processing shifts to Step S108, and a notification that there is the possibility of developing a bedsore is made. It is displayed on the display screen 34 that there is the possibility of a bedsore. When the notification unit 37 is provided, the notification may be made by light or sound or voice by the notification unit 37. Also, when the absolute value of the left-right ratio R1 is less than the predetermined value, a notification of the possibility of developing a bedsore judged to be low may be made in another form as a form of indication of a bedsore detection result.

Next, the processing shifts to Step S109, and as a weighing result, a weight of the to-be-weighed subject is displayed on the display screen 34. Step S109 may be performed along with Step S108 of indicating that there is the possibility of a bedsore.

By the weight scale 100 configured as described above, a weight of a to-be-weighed subject sitting in a wheelchair is measured, and at the same time, it can be known whether there the possibility of a bedsore and further, whether on the left side or the right side there is the possibility of developing a bedsore. In the flow of measuring a weight of a to-be-weighed subject sitting in a wheelchair, the possibility of the to-be-weighed subject developing a bedsore can be directly detected. Without needing special tools or actions, the possibility of a subject in a wheelchair developing a bedsore can be easily detected. Accordingly, a caregiver can give proper care to adjust sitting of the to-be-weighed subject.

It is also possible to configure the weight scale 100 by adding the bedsore detecting unit 39 to a conventional weight scale including four weighing sensors. Into an existing weight scale, the bedsore detecting unit 39 can also be retrofitted as a program, and the bedsore detecting function for a person in a wheelchair can be easily implemented at lower cost than by introducing specialized equipment.

(Test Data)

Figure 8:
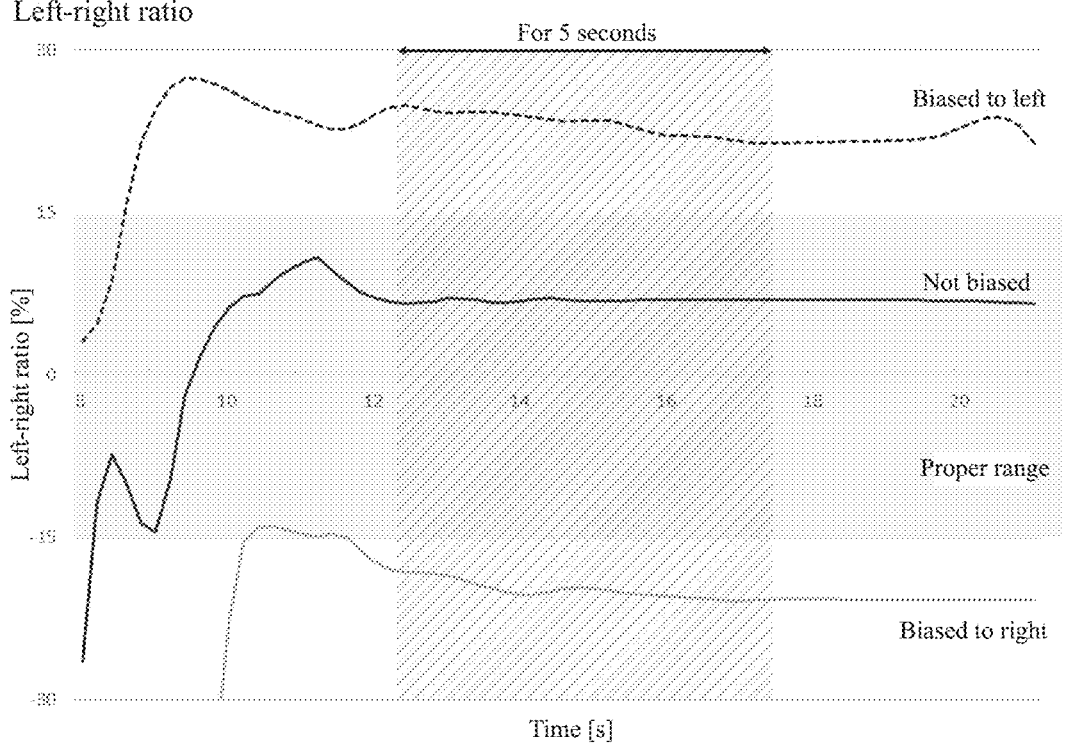
FIG. 8 is a graph of test data, illustrating left-right ratios.

FIGS. 6A to 6C, 7A to 7C, and 8 illustrate data obtained by conducting tests in actuality in which a to-be-weighed subject got on and off the weight scale 100 while sitting in a wheelchair. In order to reproduce a state where there the person in a wheelchair has a possible bedsore, data was acquired by changing the posture of the to-be-weighed subject in the wheelchair for each test. FIGS. 6A, 6B, and 6C are graphs illustrating output values W1 to W4 of the weighing sensors 42a to 42d acquired by the tests. The horizontal axis represents an elapsed time. FIG. 6A illustrates measurement data when a to-be-weighed subject got on and off the weight scale 100 while sitting with a correct posture (ideal posture) without bias on a seating surface of the wheelchair. FIG. 6B illustrates test data when the to-be-weighed subject got on and off the weight scale 100 in a state where the to-be-weighed subject sits in the wheelchair while placing his/her weight in a biased manner on the right side. FIG. 6C illustrates test data when the to-be-weighed subject got on and off the weight scale 100 in a state where the to-be-weighed subject sits in the wheelchair while placing his/her weight in a biased manner on the left side. FIGS. 7A to 7C illustrate first sum values S1 and second sum values S2 calculated based on the output values W1 to W4 acquired in FIGS. 6A to 6C. FIG. 8 illustrates left-right ratios R1 calculated based on the data acquired in FIGS. 6A to 6C. The three cases are collectively illustrated in one graph. The left-right ratio R1 on the vertical axis is expressed as percentages.

As illustrated in FIGS. 6A to 6C, when the to-be-weighed subject gets onto the weight scale 100 while sitting in a wheelchair, the weighing sensors 42a to 42d start to weigh a load, and just after the start of weighing, the output values Who W4 fluctuate, however, as the to-be-weighed subject is still on the step surface of the weighing base 20, the output values W1 to W4 converge. As the measurement values of the weighing sensors 42 become stable for a predetermined period of time, the weight scale 100 displays a weight of the to-be-weighed subject on the display screen 34. Then, as the to-be-weighed subject gets off the weighing base 200, loading on the weighing base 20 decreases, and the output values W1 to W4 decrease to zero.

When the to-be-weighed subject in a wheelchair gets on and off the weighing base 20 while being in an ideal posture, convergence values of the output values W1 to W4 are comparatively small in a difference between an upper limit value and a lower limit value as well as in a difference between the respective values (refer to FIG. 6A). On the other hand, when the to-be-weighed subject sits in the wheelchair while placing his/her weight on the right side, convergence values of the output values W1 to W4 show a tendency in which a difference between an upper limit value and a lower limit value becomes larger than that of the values in the case of the ideal posture (the values in FIG. 6A), and particularly the output values W3 and W4 of the pair of weighing sensors 42c and 42d on the right side increase (refer to FIG. 6B). Similarly, when the to-be-weighed subject sits while placing his/her weight on the left side, a tendency is shown in which the output values W1 and W2 of the pair of weighing sensors 42a and 42b on the left side increase (refer to FIG. 6C).

That is, as illustrated in FIGS. 7A to 7C, when the to-be-weighed subject is in an ideal posture (refer to FIG. 7A), the first sum value S1 and the second sum value S2 are not greatly different from each other, however, when the to-be-weighed subject sits in the wheelchair while placing his/her weight on either the left or right side (refer to FIGS. 7B and 7C), a difference occurs between the first sum value S1 and the second sum value S2, and when the weight is biased to the left side, the first sum value S1 increases, and when the weight is biased to the right side, the second sum value S2 increases.

As illustrated in FIG. 8, the value of the left-right ratio R1 becomes close to zero when the to-be-weighed subject sitting in a wheelchair is in an ideal posture without bias to the left or right, however, it greatly deviates from zero when the subject takes a posture in which placing of his/her weight is biased. The value of the left-right ratio R1 greatly varies to the positive side when placing of the weight of the to-be-weighed subject sitting in the wheelchair is greatly biased to the left side, and greatly varies to the negative side when placing of the weight of the subject is greatly biased to the right side. In the present embodiment, based on the test data, when an absolute value of the left-right ratio is less than 0.15 (less than 15%), the posture of the subject in a wheelchair is determined to be within a range of a correct posture in which a bedsore is unlikely to occur, and the range of −15% to 15% of the left-right ratio defined as a proper range is illustrated as a gray region in FIG. 8. The hatched region (partially overlapping the gray region) in FIG. 8 represents a state where the to-be-weighed subject is still and the respective values have converged for a predetermined period of time, and the predetermined period of time is set to 5 seconds in FIG. 8. The left-right ratio R1 and the weight of the to-be-weighed subject are based on values in the hatched region.

When the left-right ratio R1 is not within the predetermined value (−15% or less or 15% or more), placing of the weight of the to-be-weighed subject sitting in a wheelchair is biased, and it is judged that when the to-be-weighed subject continuously sits in the wheelchair while staying in that posture, the possibility of developing a bedsore increases (=there is the possibility of a bedsore). A configuration may be made to make it possible to set the judgment value for determining the possibility of the to-be-weighed subject developing a bedsore from the input unit 36. A configuration may be made in which the judgment value for determination is changed according to the weight of the to-be-weighed subject.

While a preferred embodiment and modifications of the present invention have been described above, the embodiments described above are just examples of the present invention, and these can be combined based on knowledge of a person skilled in the art, and such combined embodiments are also included in the scope of the present invention.

REFERENCE SIGNS LIST

20: Weighing base
38: Control unit
39: Bedsore detecting unit
42: Weighing sensor
100: Weight scale
S1: First sum value
S2 Second sum value
S3 Third sum value
W1 to W4: Output value
The invention claimed is:

1. A large weight scale configured to weigh a to-be-weighed subject sitting in a wheelchair, comprising:
a rectangular weighing base on which the to-be-weighed subject gets on;
weighing sensors disposed at four corners of the weighing base; and
a control unit configured to perform arithmetic operations based on output values of the weighing sensors,
wherein the large weight scale comprises a bedsore detecting unit configured to detect and make a notification of the possibility of the to-be-weighed subject in a wheelchair developing a bedsore based on a first sum value of output values of a pair of the weighing sensors disposed on a left side of the weighing base, a second sum value of output values of a pair of the weighing sensors disposed on a right side of the weighing base, and a third sum value of output values of all of the weighing sensors,
wherein the bedsore detecting unit is configured to determine and make a notification that there is the possibility of developing a bedsore when an absolute value of a ratio of a difference value between the first sum value and the second sum value to the third sum value exceeds a predetermined value.

2. The large weight scale according to claim 1, wherein the bedsore detecting unit is configured to make a notification as to whether there is the possibility of developing a bedsore on the left side of the body or the right side of the body, of the to-be-weighed subject in a wheelchair.

3. The large weight scale according to claim 1, wherein the bedsore detecting unit is configured to determine whether the to-be-weighed subject is in a wheelchair.

4. The large weight scale according to claim 2, wherein the bedsore detecting unit is configured to determine whether the to-be-weighed subject is in a wheelchair.

5. A bedsore detecting method as a method of detecting the possibility of a to-be-weighed subject in a wheelchair developing a bedsore by using a large weight scale provided with weighing sensors disposed at four corners of a rectangular weighing base on which a to-be-weighed subject gets on, and configured to weigh the to-be-weighed subject sitting in a wheelchair,
wherein a first sum value of output values of a pair of the weighing sensors disposed on a left side of the weighing base, a second sum value of output values of a pair of the weighing sensors disposed on a right side of the weighing base, and a third sum value of output values of all of the weighing sensors are calculated, and when an absolute value of a ratio of a difference value between the first sum value and the second sum value to the third sum value exceeds a predetermined value, it is determined and notified that there is the possibility of the to-be-weighed subject developing a bedsore.

* * * * *